United States Patent [19]

Asano et al.

[11] 4,083,733
[45] Apr. 11, 1978

[54] METHOD OF PRODUCING BETA-LACTOSE

[75] Inventors: Yusuke Asano, Kodaira; Yoshio Aoki, Higashimurayama; Nagataka Yamazaki, Yokkaichi, all of Japan

[73] Assignees: Meiji Milk Products Company Limited, Tokyo; Taiyo Kagaku Kogyo Company Limited, both of Japan

[21] Appl. No.: 744,922

[22] Filed: Nov. 26, 1976

[51] Int. Cl.$^2$ .............................................. C13K 5/00
[52] U.S. Cl. ........................................ 127/42; 127/31; 127/58; 127/63; 536/1
[58] Field of Search ........................ 127/31, 42, 58, 63

[56] References Cited

U.S. PATENT DOCUMENTS

| 1,810,682 | 6/1931 | Sharp | 127/31 |
| 1,954,602 | 4/1934 | Supplee | 127/31 |
| 1,956,811 | 5/1934 | Sharp | 127/31 |
| 2,182,618 | 12/1939 | Sharp | 127/31 |
| 2,182,619 | 12/1939 | Sharp | 127/31 |
| 3,983,862 | 10/1976 | Spriet | 127/58 |

OTHER PUBLICATIONS

Chemical Abstracts, 76:5552k(1972).

*Primary Examiner*—Sidney Marantz
*Attorney, Agent, or Firm*—Browdy and Neimark

[57] ABSTRACT

To alpha-lactose or an alpha-lactose-containing substance is added a small amount of water and the resulting mixture is subjected to extrusion from a screw extruder under pressure, thereby converting the alpha-lactose into beta-lactose. The beta-lactose or beta-lactose-containing substance thus obtained is dried, pulverized and stored as it is.

6 Claims, 1 Drawing Figure

U.S. Patent     April 11, 1978     4,083,733
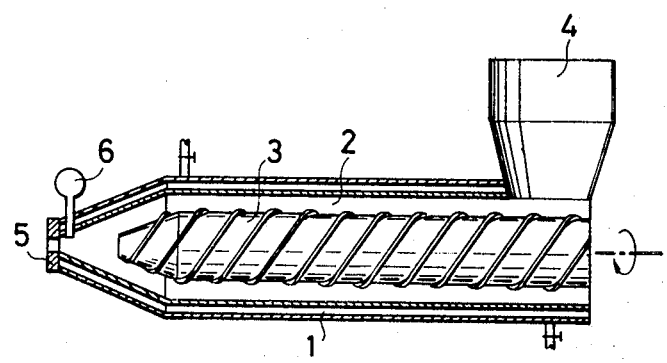

METHOD OF PRODUCING BETA-LACTOSE

The present invention relates to a method of producing beta-lactose very efficiently.

Lactose isolated from cow's milk and used widely for the production of processed foodstuffs and medicines comprises substantially alpha-lactose, beta-lactose being contained in only a very small amount. However, merits of beta-lactose in health and nutrition of infants have been found recently and, further, beta-lactose has a far higher solubility in water as compared with alpha-lactose. Under the circumstances as above, the use of beta-lactose is now increasing in amount.

Though demand of beta-lactose is thus increasing, it is very difficult to obtain stable beta-lactose of a high quality in a large amount at a low cost.

Generally, beta-lactose has been produced according to a method wherein heating is effected in a liquid and drying is effected on a drum dryer which method comprises heating an aqueous alpha-lactose solution to 93.5°–100° C and then drying the solution on a drum dryer at a temperature above 93.5° C. This process has demerits in that thermal efficiency and production efficiency are poor, a large plant is required for the mass-production, complicated operations are required and, therefore, the price of the resulting product becomes considerably high.

There has been proposed another method wherein alpha-lactose in the form of powder is stirred in steam under heating to convert it into beta-lactose. However, this method is not used practically, since it requires a long time for the treatment, conversion rate into beta-lactose is poor and a large apparatus is required. Recently, there has been proposed in Japanese Patent Lay-open No. 85746/1973 a process wherein a hydrophilic organic solvent is added to an aqueous alpha-lactose solution to form crystals at a temperature below 95° C, thereby obtaining a mixture of alpha-lactose and an increased proportion of beta-lactose. This method has also a low conversion rate into beta-lactose and requires troublesome treatments such as recovery of the organic solvent and its practicality therefore is very low.

After intensive investigations for the purpose of supplying beta-lactose of a higher quality at a lower cost, the inventors have found that alpha-lactose can be converted into beta-lactose at a high conversion rate of up to 90% by addition of a small amount of water to alpha-lactose followed by injection treatment with a simple extruder.

The present invention has been accomplished on the basis of this finding. The invention relates to a method of producing beta-lactose, characterized by adding a small amount of water to alpha-lactose or an alpha-lactose-containing substance, subjecting the same to injection under pressure using an extruder to convert alpha-lactose into beta-lactose and, if necessary, drying and pulverizing the resulting beta-lactose or beta-lactose-containing substance.

More particularly, the method of the present invention comprises adding a small amount, preferably 1.5–15 parts by weight, per 100 parts by weight of alpha-lactose or alpha-lactose-containing substance, of water to the alpha-lactose or alpha-lactose-containing substance, subjecting the mixture to pressure within an extruder and extruding the mixture therefrom to convert alpha-lactose into beta-lactose and, if necessary, drying and pulverizing the resulting beta-lactose or beta-lactose-containing substance.

Materials to be treated according to the present invention are alpha-lactose or an alpha-lactose-containing substance. Alpha-lactose may be either purified or crude product. As the alpha-lactose-containing substances, there may be mentioned dried whey, a mixture of alpha-lactose and starch and a mixture of alpha-lactose and protein.

The alpha-lactose or alpha-lactose-containing substance is added with a small amount of water. If the water is too small in amount, the mixture will be not in the form of liquid when it is brought near a die to reduce efficiency of conversion into beta-lactose and, in addition, lactose sticks to a screw to make the injection molding impossible due to excess pressure. Thus, at least 1.5%, based on the starting material, of water is required. Preferred amount of water is 2–15%, particularly 4–7%. If the water is too large in amount, for example more than 15%, beta-lactose after injection molding is in the form of slurry, it will revert to alpha-lactose if it is allowed to stand and further, a large-scaled drying treatment is required which is industrially unfavorable though the conversion into beta-lactose can be attained practically. With 4–7% of water, injection fluidity of the mixture in the extruder is quite excellent and water evaporates immediately from the injected beta-lactose or beta-lactose-containing substance obtained in the form of a slurry of a low water content, whereby the water content is reduced to 1–5% and, in addition, reconversion into alpha-lactose hardly occurs. The injected beta-lactose can be dried directly with hot air into the optimum condition for storage as beta-lactose for a long period of time.

The extruder used in the present invention may be any extruder which can be used for injection molding after compression, but a screw extruder is particularly suitable. The screw extruder comprises a screw in a cylinder which can be heated with steam, hot water or by an electric heat source in an outer jacket. By rotating the screw, alpha-lactose fed through a hopper on one side of the cylinder is moved under compression and heating and injected or ejected as beta-lactose through dies on the other side of the cylinder. It is preferred to provide a thermometer for measuring the internal temperature near the dies.

EXPLANATION OF THE DRAWINGS

The FIGURE is a cross section of an extruder used in examples of the present invention. 1 indicates a jacket, 2 indicates a cylinder, 3 indicates a screw, 4 indicates a hopper, 5 indicates a die, and 6 indicates a thermometer. Also shown are a vapor inlet and a vapor outlet to the jacket. Alpha-lactose or an alpha-lactose-containing substance is added with a small amount of water and fed into the hopper 4 and then into the cylinder 2 and it is compressed with the screw 3 while it is heated with vapor in the jacket 1. After completion of the compression and heating treatments, it is injected through the die 5.

The water added alpha-lactose or alpha-lactose-containing substance is in the form of wet powder in the hopper but it becomes a liquid as it is moved from the hopper into the central part of the cylinder by screw under compression and heating. The heating is effected through the jacket. Generally, the heating is effected at the initial stage of the operation of the extruder. Thereafter, heating is not required. Upon compression of the lactose, temperature is elevated by friction heat and compression heat, an end of the cylinder having a temperature of 100°–200° C and a pressure of 5–40 Kg/cm². Thus, alpha-lactose is converted to beta-lactose substantially completely. The pressure and temperature vary depending on type of the extruder, for example, length and pitch of the screw but they can be controlled by varying rotation velocity of the screw and feeding rate of the alpha-lactose. The lactose is moved from the hopper to the die in 3–10 seconds generally. The resulting beta-lactose is injected rapidly through the die. The major part of water in beta-lactose is evaporated out when it is brought to atmospheric pressure, leaving solids or small lumps of lactose of a low water content.

As the lactose has a lower water content immediately after the injection, deterioration in quality of the production by evaporation heat during the injection is prevented.

Consequently, the injected product does not revert to alpha-lactose and beta-lactose can be obtained at a high conversion rate. Beta-lactose thus obtained does not revert into alpha-lactose immediately because of its low water content of 1–5%. By further drying the product to a water content of less than 1%, it can be stored in a closed vessel stably for a long period of time in its beta-form.

The beta-lactose or beta-lactose-containing substance thus injected may be incorporated in a dry milk or the like and the mixture may be dried at once. In this manner, modified milk powder, baby foods, special foods for maintaining health, etc. containing beta-lactose can be produced directly.

The conversion rate into beta-lactose according to the present invention, which is determined by gas chromatography, can be controlled at will by varying extruding pressure of the extruder. As compared with a conventional process, by effecting the treatment under a high pressure according to the present invention, a far higher conversion rate into beta-lactose of around 90% and an excellent quality can be attained and, in addition, mass production of beta-lactose is facilitated with the extruder and, therefore, beta-lactose can be supplied stably at a low cost. Thus, if the beta-lactose is to be used for the production of modified milk powder, the process of the invention is of great advantage with respect to quality and economy. Beta-lactose is superior to alpha-lactose in solubility and sweetness and the former has excellent disintegrating and binding properties. Thus, if beta-lactose is used as vehicles, it contributes greatly to improvement in quality of tablets of medicines.

Experimental examples of the invention will be shown below:

EXPERIMENTAL EXAMPLE 1

Relationship between treatment temperature or pressure and conversion rate into beta-lactose was determined by treating alpha-lactose of water content of 5% with an extruder of type X 25 of Wenger Manufacturing Company, U.S.A.

The results were as shown in Table 1. Table 1 indicates that if sample temperature is raised to 135° C under elevated treatment pressure, conversion is 60% and that the conversion is increased as the treatment pressure is elevated.

Table 1

| No. | Sample temp.* (° C) | Treatment Pressure (Shown in amperes) | Conversion** (%) |
|---|---|---|---|
| 1 | 135 | 65A(8–10 Kg/cm²) | 60 |
| 2 | 140 | 80A(10–13 Kg/cm²) | 70 |
| 3 | 150 | 100A(13–15 Kg/cm²) | 80 |
| 4 | 165 | 120A(15–17 Kg/cm²) | 90 |

*Measured at an end of extruder.
**Measured by gas chromatography

EXPERIMENTAL EXAMPLE 2

Relationship between treatment temperature or pressure and conversion rate into beta-lactose to which varied amounts in the range of 5–15% of water were added and which was treated with the same extruder as in Experimental Example 1 was determined. The results are shown in Table 2.

Table 2

| No. | Water added (%) | Sample temp. (° C) | Treatment pressure (shown in amperes) | Conversion (%) | Water content at the discharge from extruder (%) |
|---|---|---|---|---|---|
| 5 | 5 | 150 | 100A(about 15 Kg/cm²) | 80 | 1.5–2.0 |
| 6 | 10 | 120 | 40A(about 3 Kg/cm²) | 30 | 4.8–6.7 |
| 7 | 15 | 110 | 20A(1–2 Kg/cm²) | 15 | 8.5–9.0 |
| 6' | 10 | 120 | 40A | 40* | Same as No. 6 |
| 7' | 15 | 110 | 20A | 50* | Same as No. 7 |

*Conversions into beta-lactose in Runs Nos. 6'and 7' were obtained by drying samples obtained in Runs Nos. 6 and 7 while they were kept at a temperature above 93.5° C immediately after discharge from the extruder and then determining the values.

It is apparent from Table 2 that with 5% of water added, a high conversion rate of up to 80% can be attained and water content of the lactose is reduced to 1.5–2.0% when it is discharged from the extruder to the atmosphere, thereby hardly reducing the conversion rate. However, with a large amount of water added, it is considered that the conversion rate is low for two reasons of (1) conversion into beta-form is not complete due to difficulty of elevation of the pressure in the extruder and (2) re-conversion of beta-lactose into alpha-lactose due to a high water content thereof after being discharged from the extruder.

The following example further illustrates the present invention.

EXAMPLE

Steam was introduced in a jacket of an extruder (extruder X 25 of Wenger Manufacturing Company, U.S.A.). When temperature at an end of the cylinder reached 160° C, the introduction of steam was stopped. A mixture of 100 parts of alpha-lactose and 5 parts of water was fed therein through a hopper at a rate of about 100 Kg/hr. at a rotation velocity of screw of about 100 r.p.m. Beta-lactose was injected immediately thereafter through a die. Temperature at the end of cylinder was kept at 170° C by controlling amount of alpha-lactose to be fed and rotation velocity of the screw. Pressure was about 15 Kg/cm$^2$. Beta-lactose thus injected continuously had a water content of 1.8% and a conversion rate of 90%. The beta-lactose was further dried at 60°–80° C to a water content of 0.5%.

After storage of the resulting dry beta-lactose in a closed vessel under dry condition for 1 month, no change in quality was observed.

What is claimed is:

1. A method of producing beta-lactose comprising adding a small amount of water to an alpha-lactose material selected from the group consisting of alpha-lactose and alpha-lactose-containing substances and subjecting the resulting mixture to extrusion from a screw extruder under pressure to convert the alpha-lactose into beta-lactose.

2. A method of producing beta-lactose comprising adding a small amount of water to an alpha-lactose material selected from the group consisting of alpha-lactose and alpha-lactose-containing substances, subjecting the resulting mixture to extrusion from a screw extruder under pressure to convert the alpha-lactose into beta-lactose and drying and pulverizing the resulting extruded product.

3. A method of producing beta-lactose comprising adding water to an alpha-lactose material selected from the group consisting of alpha-lactose, dried whey, a mixture of alpha-lactose and starch and a mixture of alpha-lactose and protein, said water being 1.5–15% by weight of the alpha-lactose material, and subjecting the resulting mixture to extrusion from a screw extruder at 100°–200° C under a pressure of 5–40 Kg/cm$^2$ to convert the alpha-lactose into beta-lactose.

4. A method in accordance with claim 3 wherein 4–7% of said water is used.

5. A method of producing beta-lactose comprising adding water to an alpha-lactose material selected from the group consisting of alpha-lactose, dried whey, a mixture of alpha-lactose and starch and a mixture of alpha-lactose and protein, said water being 1.5–15% by weight of the alpha-lactose material, subjecting the resulting material to extrusion from a screw extruder at 100°–200° C under a pressure of 5–40 Kg/cm$^2$ to convert the alpha-lactose into beta-lactose and drying and pulverizing the resulting extruded product.

6. A method in accordance with claim 5 wherein 4–7% of said water is used.

* * * * *